(12) United States Patent
Ruefer et al.

(10) Patent No.: US 7,794,576 B2
(45) Date of Patent: Sep. 14, 2010

(54) PROTEIN RESOLUTION ENHANCEMENT BY USING MATRIX CONTAINING DMSO

(75) Inventors: Andreas Ruefer, Karlsruhe (DE); Martin Kratzmeier, Waldbronn (DE)

(73) Assignee: Agilent Technologies, Inc., Santa Clara, CA (US)

(*) Notice: Subject to any disclaimer, the term of this patent is extended or adjusted under 35 U.S.C. 154(b) by 1327 days.

(21) Appl. No.: 11/150,079

(22) Filed: Jun. 10, 2005

(65) Prior Publication Data

US 2006/0021876 A1 Feb. 2, 2006

(30) Foreign Application Priority Data

Jul. 30, 2004 (EP) .................. 04103683

(51) Int. Cl.
*G01N 27/447* (2006.01)
*C07K 1/26* (2006.01)

(52) U.S. Cl. .................. 204/469; 204/470; 204/465; 204/456; 204/461; 204/450

(58) Field of Classification Search ......... 204/450–470, 204/157.6, 600–618
See application file for complete search history.

(56) References Cited

U.S. PATENT DOCUMENTS

| | | | |
|---|---|---|---|
| 4,819,645 A * | 4/1989 | Peck | 600/362 |
| 5,290,411 A * | 3/1994 | Zewert et al. | 204/606 |
| 6,475,364 B1 * | 11/2002 | Dubrow et al. | 204/455 |

FOREIGN PATENT DOCUMENTS

| | | |
|---|---|---|
| WO | WO 95/18813 | 7/1995 |
| WO | WO 00/67009 | 11/2000 |
| WO | WO 02/055662 | 7/2002 |
| WO | WO 02055662 A2 * | 7/2002 |

OTHER PUBLICATIONS

Li et al., Effects of gel matrial on fluorescence lifetime detection of dyes and dye-labeled DNA primers in capillary electrophoresis, Journal of Chromatography A, vol. 841, Feb. 18, 1999, pp. 95-103.*
Zewert, Thomas et al, "Polyethyleneglycol methacrylate 200 as an electrophoresis matrix in hydroorganic solvents", Electrophoresis 1992, vol. 13, pp. 824-831.

(Continued)

*Primary Examiner*—Alexa D Neckel
*Assistant Examiner*—Jennifer Dieterle

(57) ABSTRACT

An electrophoresis gel matrix is provided for conducting proteomics, in particular the steps of separating and/or identifying proteins. The matrix comprises at least one chemical reagent being at least one of a denaturing, buffering, disaggregating, reducing, staining or dissolving reagent, and a volume of dimethylsulfoxide. The use of such a matrix, which is provided to be filled into an electrophoresis capillary being part of a microfluidic device for carrying out proteomics, leads to an enhanced resolution of proteins. The matrix is prepared adding a volume of dimethylsulfoxide ranging from 4% to 15%, preferably from 5% to 10%, most preferably from 6% to 8% with respect to the total volume of chemical reagents being comprised in the matrix. A method is provided for preparation of the matrix for conducting proteomics and a method is conducted to carry out proteomics by the use of this matrix.

12 Claims, 5 Drawing Sheets

OTHER PUBLICATIONS

Zwert, Thomas et al, "Polyhydroxy and Polyethleneglycol (Meth) Acrylate Polymers: Physical Properties and General Studies for their use as Electrophoresis Matrices", Electrophoresis 1992, vol. 13, pp. 817-824.

Artoni, G. et al "Fractionation Techniques in a Hydro-Organic Environment II. Acryloyl-Morpholine Polymers as a Matrix for Electrophoresis in Hydro-Organic Solvents", Analytical Biochemistry, vol. 137, Issue 2, Mar. 1984, pp. 420-428.

Zhang, Jian et al, "Capillary electrophoresis of proteins in dextran-coated columns", Electrophoresis, vol. 24, No. 1, Jan. 2003, pp. 115-120.

Venter, J.C. et al., "The Sequence of the Human Genome", Science, Feb. 16, 2001, vol. 291, pp. 1304 ff.

EP Search Report, Nov. 24, 2004.

* cited by examiner

Low Molecular Weight Proteins

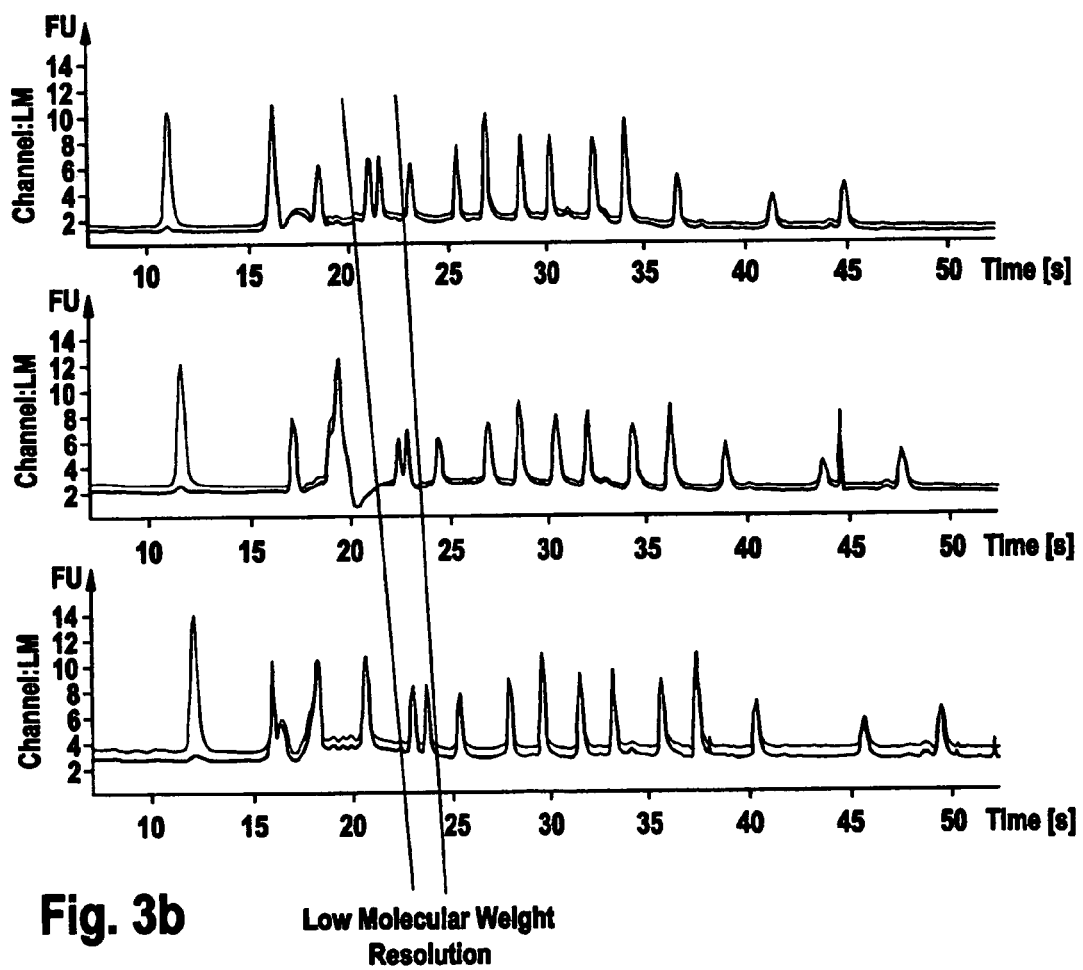
Fig. 3b  Low Molecular Weight Resolution

PROTEIN RESOLUTION ENHANCEMENT BY USING MATRIX CONTAINING DMSO

The present invention relates to an electrophoresis gel matrix providing an enhanced resolution of proteins in microfluidic separation assays.

In order carry out proteomics aiming for a complete analysis of the total amount of the proteins expressed by a genome the sample of interest has to be subjected to the following steps:

In a first step preparation of the biological material has to be done, which means that the proteins have to be extracted. In a conventionally performed second step the proteins are separated by two dimensional electrophoresis before a third step results in spot identification which has in the past mostly been done by mass spectrometry after hydrolysis of the protein. Finally, identification of the complete protein sequence takes place, being supported by database search.

The separation step (second step) comprises a first dimension, subjecting the amphoteric proteins to isoelectric focusing. Accordingly, the separation of the molecules is related to their isoelectric point. The second dimension of this separation step is conventionally the SDS-PAGE, wherein proteins are separated according to their size. Sodiumdodecylsulfate SDS is an anionic detergent that is electrically charged. Since the charge of the proteins exceeds the charge of the SDS, anionic micelles are composed, having a substantially constant net-charge per mass unit. Furthermore hydrogen bonds are split, thus dissolving tertiary and secondary structures of the protein molecules. Disulfide bridges can be dissolved by adding thiol compounds with reducing properties, and adding urea causes denaturing of the sample.

Ideally, the sample is being disaggregated, denatured, reduced and completely dissolved after preparation. Adding of dithiothreitol (DDT) to the buffer helps disturbing disulfide bridges and keeps the proteins in the reduced state.

The above SDS separation can be performed by capillary electrophoresis, in analogy to the application of capillary electrophoresis to sequence genomes. (See: Venter, J. C. et al., Science 2001, 291, pp 1304 ff.). For separation, a micro device containing a separation gel with sieving properties is used. It is filled into a channel of the micro device, thus providing a separation channel.

Subsequent to the separation identification is carried out. The conventional SDS-page is mostly followed by MALDI-TOF-MS (Matrix Assisted Laser Desorption Ionization Time Of Flight Mass Spectrometry). Other identification techniques such as optical techniques or techniques basing on electrolytic sensing are known in the art.

After all, the preparation of the electrophoresis gel that is used in the second step is the clue to successful separation and subsequent identification. The electrophoresis gel or the separation matrix, respectively, must have optimal sieving properties with respect to the reagents to be applied on it as well as with respect to its ability for being filled into micro channels for capillary electrophoresis applications. It is desirable that the electrophoresis gel matrix is storable for a certain time without ageing, since ageing is mostly followed by a loss of separation efficiency.

DISCLOSURE OF THE INVENTION

It is an object of the invention to provide an electrophoresis gel matrix for conducting proteomics showing an enhanced protein resolution. The object is solved by the independent claims. Preferred embodiments are shown by the dependent claims.

It has been found that capillary electrophoresis is an appropriate method to perform proteomics in an economic way, in particular with respect to separation and identification of proteins, which are the steps of interest in the present invention. Concerning the time and the volume of sample material to be expended for SDS PAGE, capillary electrophoresis is a most economic and efficient method. Carried out in a microfluidic device, thus being linearly performed, a sample volume of only a few micro liters is required, being passed through the separation channel of the microfluidic device in about three hours: The time needed for the passage is depending on the size of the protein molecules to be sieved.

Linear capillary electrophoresis being performed in a microfluidic device requires a microfluidic channel as capillary being filled with an appropriate electrophoresis gel matrix. In the present invention a Poly-N,N-Dimethylacrylamide (PDMA) matrix is suggested for conducting proteomics but, of course, other matrix materials such as Dextran, linear Polyacrylamide, Poly-N-Acryloylaminoethoxyethanol (PAAEE), Polyacryloylaminopropanol (PMP), Poly-(acryloylaminoethoxy)ethyl-glucopyranoside (PAEG), Polyethylene Glycol (PEG), Polyethyleneoxide (PEO), Polyvinyl pyrolidone (PVP) or cellulose materials like Methylcellulose (MC), Hydroxyethylcellulose (HEC), Hydroxypropylcellulose (HPC), Hydroxypropyl-methylcellulose (HPMC) may be selected, only to name some of the more popular materials.

The filling procedure is performed under high pressure due to the viscosity of the PDMA matrix, which may be done automatically (5100 ALP prototype, Agilent Technologies) or in a manual filling station (2100 Bioanalyzer, Agilent Technologies).

Prior to the filling, the matrix has to be prepared in a way that the desired separation or sieving step becomes performable:

Chemical reagents such as a denaturing, disaggregating, reducing, staining or dissolving reagents are added to the electrophoresis gel matrix, herein made from PDMA, which has a linear structure. The denaturing reagent can be preferably sodiumdodecylsulfate (SDS), as dissolving and reducing reagents thiol containing compounds could be selected. In order to buffer the system which results from giving the above chemical reagents to the PDMA matrix a buffer as tris tricine or the like can be added. The system may be buffered to a pH of 7.6, preferably.

To perform a visualization of the protein molecules to be sieved, a staining reagent can optionally be given to the solution. Then, applying an optical active dye such as a fluorescent dye as protein staining reagent is desirable, permitting an optical detection of the proteins when leaving the electrophoretic separation channel.

Conventional organic dyes, in particular fluorescent dyes that are used frequently in the art, are badly soluble or instable in water or aqueous solutions, accordingly they are stored in organic solvents. Dimethylsulfoxide (DMSO) is an aprotic and polar reagent being an optimal solvatizing reagent for numerous organic dyes, in particular for those being used as staining reagents for proteomics.

It is known in the art that DMSO on the other hand is sustaining and negatively influencing the electrophoresis gel matrix, providing an accelerated ageing of the matrix. Accordingly scientists therefore apply the staining dye freed from DMSO.

Meanwhile there are staining dyes available that provide a good solubility in water or aqueous solutions and remain stable when stored in an aquatic system. This permits the use of staining dyes that are initially free from DMSO, thus preventing an accelerated ageing of a matrix prepared for proteomics.

The present invention is therefore based on the discovery of a novel technical effect of DMSO used in electrophoretic methods applied to carry out the separation step and to permit an optimal identification in proteomics. The invention comprises the use of DMSO as a resolution enhancing chemical reagent in the PDMA matrix that is prepared as described above. It is the specific intention of the present invention to enhance the resolution of protein molecules, in particular of low molecular weight molecules, being separated in a microfluidic device by use of capillary electrophoresis in a linear PDMA matrix.

In order to obtain the resolution effect as described above, an embodiment of the capillary electrophoresis matrix used in microfluidic devices for performing the separation step in the proteomics process with subsequent identification of the separated proteins comprises a PDMA gel matrix which is prepared as described above, at least one of the denaturing, disaggregating, reducing, staining or dissolving reagents indicated above being added, wherein DMSO is comprised. DMSO is added to the reagents composing the matrix in an extra step, guaranteeing that at least a volume of 4% DMSO with respect to the total volume of chemical reagents being comprised in the matrix is contained. The examples depicted below show clearly that the addition of a volume DMSO over 4% is desirable, preferably an amount of about 6% DMSO with respect to the total volume of reagents can be added. Generally, the low molecular weight resolving power of the gel matrix is increasing the more DMSO was added to the matrix before. But, expectedly, the overall analysis time, meaning the time from sample injection into the separation channel until detection of the largest protein (also referred to as upper marker or UM) is increasing as well.

Thus, using dimethylsulfoxide in PDMA matrices for separating and/or identifying proteins leads to an enhancement of the resolving power of PDMA gel matrices prepared according to the present invention. An optimization of the resolution takes place, leading furthermore to a better identification of the proteins. Identification of the proteins can be carried out by measuring an identifying parameter which can be any physical or chemical parameter permitting a unique identification of the protein.

Accordingly, it is easy to be understood that the enhancement of the resolution provided by the application of DMSO in a matrix according to the present invention is completely independent on the presence of a staining dye, though visualization of the resolution is facilitated by application of a dye.

In order to test for an enhanced resolution or to show that single proteins, in particular low molecular weight proteins, are separated much clearer from neighboring proteins, respectively, according to the-present invention, optical detection techniques such as laser induced fluorescence (LIF) or any appropriate detection technique such as fluid conductivity or the like can be applied.

The method for carrying out separation and identification of proteins according to the present invention thus comprises firstly the preparation of an electrophoresis gel matrix for conducting micro-channel separation of proteins, or "proteomics" in the broad sense. In order to do so the chemical reagents selected from the group of denaturing, buffering, disaggregating, reducing, staining or dissolving reagents are added to a PDMA gel, together with a volume of dimethylsulfoxide.

BRIEF DESCRIPTION OF DRAWINGS

The objects and the attendant advantages of the present invention will be readily appreciated and become better understood by reference to the following Figures.

FIG. 3b shows the influence of methyl urea and DMSO addition to gel-matrix on assay performance in terms of low molecular weight proteins resolution.

EXPERIMENTS

Example I

Figure 1A:
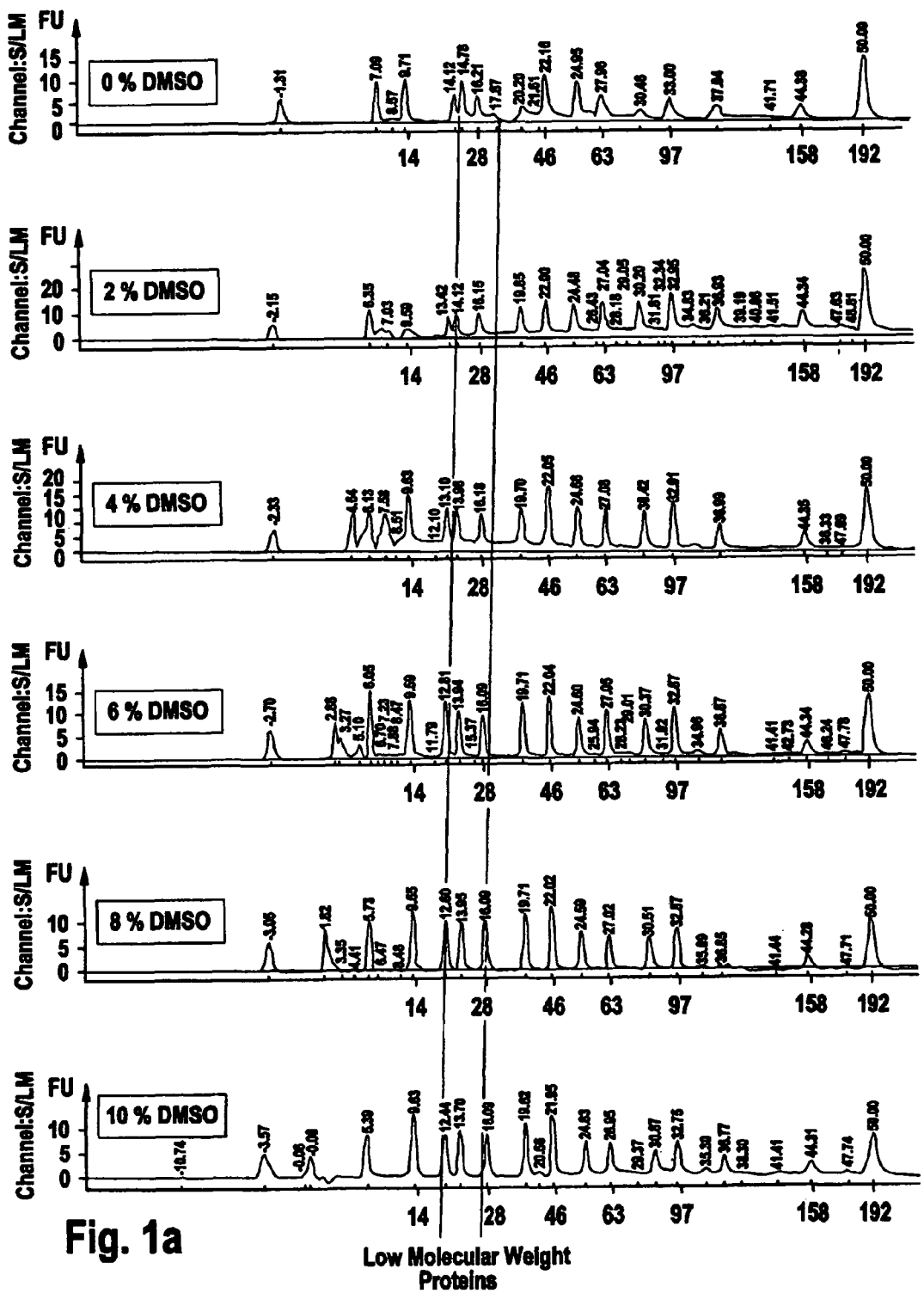
FIG. 1a shows the results of a series of protein standard measurements with increasing DMSO concentration in the matrix, using the 5100 ALP system.
Figure 1B:
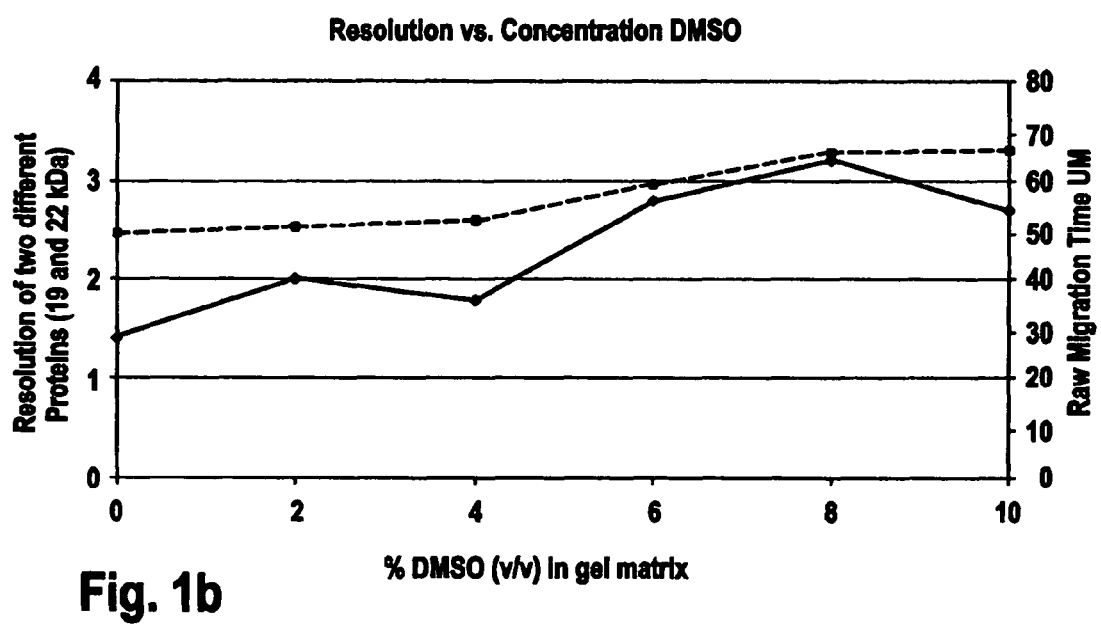
FIG. 1b shows the results of a series of protein standard measurements with increasing DMSO concentration in the matrix in relation to the analysis time, using the 5100 ALP system.

FIGS. 1a and 1b refer to the following experimental set up: The experiments were conducted by using the following analysis instruments: 5100 ALP (prototype Agilent Technologies) in combination with a Protein 200 HT$^2$ assay (prototype, Agilent Technologies) and the appropriate microfluidic chip (Protein 200 HT$^2$ chip, manufactured by Caliper Life Sciences, Inc.).

In the following description of experiments and results "analysis" time is to be understood as the time from sample injection into the separation channel until detection of the largest protein, which is also referred to as "upper marker" (UM).

Matrix Preparation:

The electrophoresis gel matrices have been prepared using:
PDMA as matrix gel, 6.5% w/v solids, manufactured by Polysciences, Inc., Art. 12514
0.25% (w/v) SDS for protein denaturing
fluorescent staining dye
120 mM tris-tricine buffering solution.
DMSO: 1.) 0%; 2.) 2%; 3.) 4%; 4.) 6%; 5.) 8%; 6.) 10%, with respect to the total volume of reagents.

The matrices prepared with the above reagents have been buffered to a pH of 7.6. Filling the matrices into the electrophoresis capillaries of the microfluidic chip is performed fully automated by the liquid-handling and pressure systems of the 5100 ALP instrument.

Sample Preparation:

The protein samples have been heat denatured with SDS at 95° C for 5 min, then they have been diluted with water ⅕ fold. Loading the samples onto the chip has been performed in a fully automated procedure. Each sample has been moved through the electrophoresis capillary, thus, through the separation channel, respectively, in order to separate the proteins contained therein. After the separation a destaining step is performed when the sample leaves the separation channel.

Identification of the Proteins:

The identification of the protein has been done subsequent to the destaining step by laser-induced fluorescence (LIF). Data is collected, processed and stored by the 5100 ALP software (prototype, Agilent Technologies).

Results

The analysis of protein standards according to the above experimental set up depicted in FIG. 1a shows the resolution capacity as a function of the DMSO content of the gel matrix. From repeating analysis of one particular protein standard sample one can see that with an increasing concentration of DMSO in the PDMA gel matrix, the resolving power of the separation is enhanced. Within the low molecular weight range the increasing resolution power with increasing. DMSO concentration can readily be detected visually: See dotted vertical lines in FIG. 1.

FIG. 1b confirms the visual impression of FIG. 1: The corresponding resolution of the system for the two protein peaks of roughly 19 kDa and 22 kDa size (as indicated in FIG. 1a, dotted vertical lines) has been calculated by the following formula:

$$Resolution = 2 \cdot (t2-t1)/(w1+w2)$$

with t1 and t2: raw migration time of peak 1 and 2
w1 and w2: temporal peak width.

The results shown above are average resolution values from 12 independent runs per DMSO concentration. It can clearly be seen that, the low molecular weight resolving power of the gel matrix is increasing the more DMSO was added to the matrix before while the overall analysis time is increasing. The optimum with reference to both, separation speed and separation power has been reached at 6% DMSO added to the standard 6.5% PDMA gel matrix.

Example II

Figure 2:
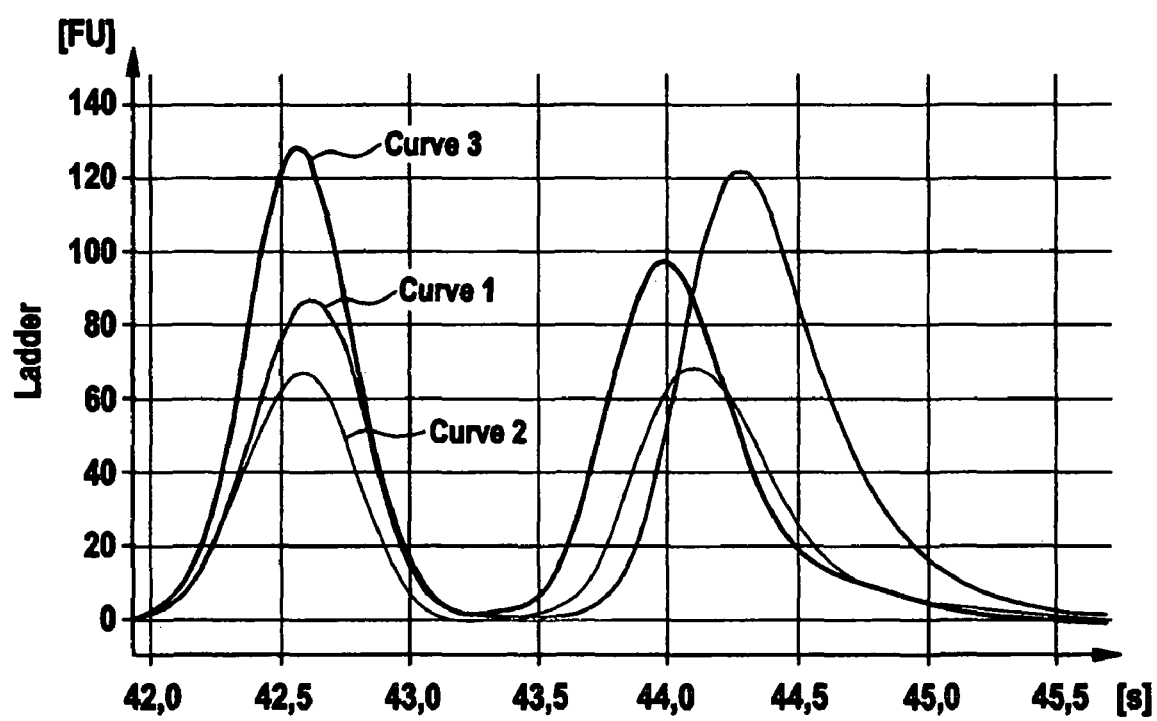
FIG. 2 shows the results of a series of protein standard measurements with increasing DMSO concentration in the matrix, using the 2100 Bioanalyzer system.

FIG. 2 refers to the following experimental set up:

The experiments were conducted by using the following analysis instruments: 2100 Bioanalyzer (prototype Agilent Technologies) in combination with a Protein 50 assay (prototype, Agilent Technologies) and an appropriate microfluidic chip.

Matrix Preparation:

The electrophoresis gel matrices have been prepared using:
  PDMA as matrix gel, 6.5% w/v solids, manufactured by Polysciences, Inc., Art. 12514
  0.25% (w/v) SDS for protein denaturing
  fluorescent staining dye
  120 mM tris-tricine buffering solution
  methyl-urea
  DMSO: 1.) 4%; 2.) 6%; 3.) 8%; with respect to the total volume of reagents.

The matrices prepared with the above reagents have been buffered to a pH of 7.6. Filling the matrices into the electrophoresis capillaries of the microfluidic device has been done using the standard 2100 Bioanalyzer manual priming station.

Sample Preparation:

The protein samples have been heat denatured with SDS at 95° C. for 5 min, then they have been diluted with water ⅟₁₅ fold. Loading the samples onto the chip has been performed manually. Each sample has been moved through the electrophoresis capillary, thus, through the separation channel, respectively, in order to separate the proteins contained therein. After the separation a destaining step is performed when the sample leaves the separation channel.

Identification of the Proteins:

The identification of the protein has been done subsequent to the destaining step by use of laser-induced fluorescence (LIF). Corresponding electropherograms are captured, processed, and stored by the 2100 Expert Software (Agilent Technologies).

Results

FIG. 2 shows three-curves of electropherograms being captured, processed, and stored by the 2100 Expert Software (Agilent Technologies). Experiments with three samples from one protein standard (Protein standards ladder, custom made for Agilent Technologies (Fermentas AB)) were conducted. Each sample has been separated with another matrix, the matrices containing 4%, 6% and 8% of DMSO. It can bee seen that the signals resulting from two proteins are separated the clearer, the more DMSO is contained in the matrix:
Curve 1, obtained with a matrix containing 4% DMSO: the first peak maximum resulting from protein 1 has been measured at about 42.6 s, the second peak maximum resulting from protein 2 has been measured at about 43.9 s, a difference of approximately 1.3 s separating the peaks.
Curve 3, obtained with a matrix containing 8% DMSO: the first peak maximum resulting from protein 1 has been measured at about 42.55 s, the second peak maximum resulting from protein 2 has been measured at about 44.3 s, a difference of approximately 1.95 s separating the peaks.
The intensities of the signals are not related to the resolution they rather reflect normal fluctuations in sample loading and processing towards the separation channel. An enhancement of the resolution can be seen clearly.

Accordingly, despite of the use of two different microfluidic systems similar results were obtained in examples I and II.

In examples I and II (and II, see below) DMSO has generally improved the resolving power of PDMA gel matrices, independent of their strength and other additives added.

Example III

Figure 3A:
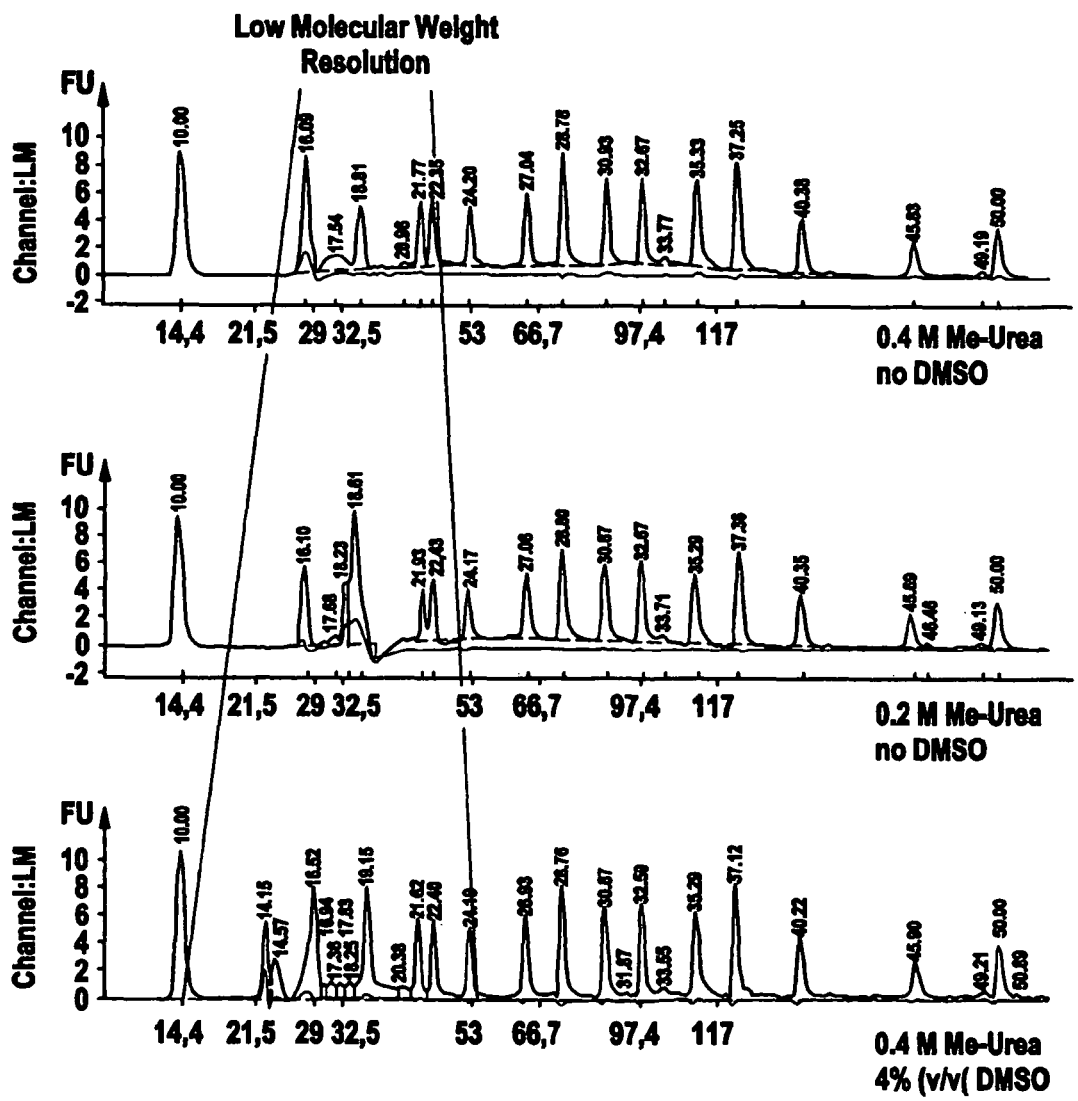
FIG. 3a shows the results of protein sample separation being methyl urea or methyl urea and DMSO influenced, using the 5100 ALP system.

FIGS. 3a and 3b refer to the following experimental set up:

The experiments were conducted by using the following analysis instruments: 5100 ALP (prototype Agilent Technologies) in combination with a Protein 200 HT. assay (prototype, Agilent Technologies) and the appropriate microfluidic chip (Protein 200 $HT^2$ chip, manufactured by Caliper Life Sciences, Inc.).

Matrix Preparation:

The electrophoresis gel matrices have been prepared using:
  PDMA as matrix gel, 6.5% w/v solids, manufactured by Polysciences, Inc., Art. 12514
  0.25% (w/v) SDS for protein denaturing
  0.25% (vol.) SDS for protein denaturing)
  fluorescent staining dye
  120 mM tris-tricine buffering solution
  Matrix provided with: 1.) 0.4 M methyl-urea solution %; 2.) 0.2 M methyl-urea solution 3.) 0.2 M methyl-urea solution and 4% DMSO (with respect to the total volume of reagents).

The matrices prepared with the above reagents have been buffered to a pH of 7.6. Filling the matrices into the electrophoresis capillaries of the microfluidic device has been done in a fully automated procedure.

Sample Preparation:

The protein samples have been heat denatured with 1% SDS at 95° C. for 5 min, then they have been diluted with water ⅕ fold. Loading the samples onto the chip has been performed in a fully automated procedure. Each sample has been moved through the electrophoresis capillary, thus, through the separation channel, respectively, in order to separate the proteins contained therein. After the separation a destaining step is performed when the sample leaves the separation channel.

Identification of the Proteins:

The identification of the protein has been done subsequent to the destaining step. Data is acquired, processed and stored by the 5100 ALP software (prototype, Agilent Technologies).

Results

FIG. 3a gives a visual impression for the enhancement of resolution for low molecular weight (MW) proteins. Three samples from a protein standards ladder (Fermentas AB) have been separated by using the above describes matrix, provided with:

1.) 0.4 M methyl-urea solution; curve 1,
2.) 0.2 M methyl-urea solution; curve 2,
3.) 0.2 M methyl-urea solution and 4% DMSO; curve 3.

The third curve indicates that adding of DMSO leads to a significant enhancement in resolution. This has been proved by calculating the resolution according to the formula given below for one example shown in FIG. 3b, thus pointing out a detail of FIG. 3a:

Resolution=$2 \cdot (t2-t1)/(w1+w2)$ with t1 and t2: raw migration time of peak 1 and 2
w1 and w2: temporal peak width.

|  | Me-Urea | DMSO | Low MW Resolution* |
|---|---|---|---|
| Curve 1 | 0.4 M | 0 | 0.89 |
| Curve 2 | 0.2 M | 0 | 0.84 |
| Curve 3 | 0.2 M | 4% (v/v) | 1.26 |

The resolution of the analyzed peaks, marked with vertical lines in FIG. 3b, curve 3, is approximately 1.5 times higher than the resolution obtained by use of DMSO free matrices (curves 1 and 2).

The invention claimed is:

1. A method for preparing an electrophoresis gel matrix, the method comprising:
   adding to an electrophoresis gel matrix a tris-tricine buffering reagent;
   a sodiumdodecylsulfate denaturing reagent;
   a dissolving or reducing reagent which is a thiol containing compound;
   a fluorescent dye staining reagent; and
   a volume of dimethylsulfoxide, wherein 6% to 8% of dimethylsulfoxide is added to the electrophoresis gel with respect to the total volume of chemical reagents being comprised in the gel matrix.

2. The method of claim 1, wherein the fluorescent dye is one or more of water soluble or stable in aqueous solutions.

3. The method of claim 1, wherein the electrophoresis gel matrix comprises Poly-N, N-Dimethylacrylamide (PDMA), Methylcellulose (MC), Hydroxyethylcellulose (HEC), Hydroxypropylcellulose (HPC), Hydroxypropylmethylcellulose (HPMC), Dextran, linear Polyacrylamide, PolyNAcryloylaminoethoxyethanol (PAAEE), Polyacryloylaminopropanol (PAAP), Poly(acryloylaminoethoxy)ethylglucopyranoside (PAEG), Polyethylene Glycol (PEG), Polyethyleneoxide (PEO) or Polyvinyl Pyrrolidone (PVP).

4. An electrophoretic method comprising:
   adding to an electrophoresis gel matrix at least one chemical reagent being at least a denaturing, buffering, disaggregating, reducing, staining or dissolving reagent,
   adding a volume of dimethylsulfoxide to an electrophoresis gel matrix; and
   separating and/or identifying proteins using the electrophoresis gel matrix.

5. The method of claim 4, wherein when the chemical agent is a buffering reagent, the buffering reagent is a tris-tricine buffer and when the chemical agent is a denaturing agent, the denaturing reagent is sodiumdodecylsulfate and when the chemical agent is a dissolving or reducing agent, the dissolving or reducing reagent is a thiol containing compound and when the chemical agent is a staining agent, the staining reagent is a fluorescent dye.

6. The method of claim 5, wherein the fluorescent dye is one or more of water soluble or stable in aqueous solutions.

7. The method of claim 4, wherein separating and/or identifying proteins comprises optically detecting the proteins.

8. The method of claim 4, wherein separating and/or identifying proteins comprises using fluid conductivity measurements to detect the proteins.

9. The method of claim 4, wherein a volume of dimethylsulfoxide is added to the matrix which ranges from 5% to 10% with respect to the total volume of chemical reagents being comprised in the matrix.

10. The method of claim 4, wherein a volume of dimethylsulfoxide is added to the matrix which ranges from 6% to 8% with respect to the total volume of chemical reagents being comprised in the matrix.

11. The method of claim 4, further comprising adding to the matrix one or more of: sodiumdodecylsulfate to denature proteins, tis-tricine to buffer the matrix, thiol containing compound to dissolve and reduce proteins, or a fluorescent dye to stain proteins.

12. The method of claim 4, wherein the electrophoresis gel matrix comprises Poly-N, N-Dimethylacrylamide (PDMA), Methylcellulose (MC), Hydroxyethylcellulose (HEC), Hydroxypropylcellulose (HPC), Hydroxypropylmethylcellulose (HPMC), Dextran, linear Polyacrylamide, PolyNAcryloylaminoethoxyethanol (PAAEE), Polyacryloylaminopropanol (PAAP), Poly(acryloylaminoethoxy)ethylglucopyranoside (PAEG), Polyethylene Glycol (PEG), Polyethyleneoxide (PEO) or Polyvinyl Pyrrolidone (PVP).

* * * * *